United States Patent
Outlaw et al.

(10) Patent No.: US 11,925,813 B1
(45) Date of Patent: Mar. 12, 2024

(54) INTERSTITIAL PHOTODYNAMIC THERAPY PROBE DELIVERY DEVICE

(71) Applicant: Lumeda inc, Rocky Hill, CT (US)

(72) Inventors: Bryan Outlaw, Broad Brook, CT (US); Trevor MacDougall, South Dartmouth, MA (US)

(73) Assignee: Lumeda Inc., Rocky Hill, CT (US)

( * ) Notice: Subject to any disclaimer, the term of this patent is extended or adjusted under 35 U.S.C. 154(b) by 0 days.

(21) Appl. No.: 18/255,226

(22) PCT Filed: Jan. 4, 2023

(86) PCT No.: PCT/US2023/060070
§ 371 (c)(1),
(2) Date: May 31, 2023

(51) Int. Cl.
*A61N 5/06* (2006.01)

(52) U.S. Cl.
CPC .......... *A61N 5/0601* (2013.01); *A61N 5/062* (2013.01); *A61N 2005/0612* (2013.01); *A61N 2005/063* (2013.01)

(58) Field of Classification Search
CPC .............. A61B 18/22; A61B 2018/225; A61B 2017/22087; A61N 5/062; A61K 41/0057
See application file for complete search history.

(56) References Cited

U.S. PATENT DOCUMENTS

| | | | |
|---|---|---|---|
| 2008/0249517 | A1 | 10/2008 | Svanberg |
| 2010/0152533 | A1 | 6/2010 | Mark |
| 2015/0273236 | A1 | 10/2015 | Rogers |
| 2019/0290314 | A1 | 9/2019 | Gemer |

FOREIGN PATENT DOCUMENTS

WO      1993004727 A1      3/1993

*Primary Examiner* — Deanna K Hall
(74) *Attorney, Agent, or Firm* — Matthew J Patterson

(57) ABSTRACT

In some implementations, a PDT delivery device is disclosed that may include a housing including a handle, a fiber lock orifice, a probe insertion orifice and a tube retraction groove positioned between the fiber lock orifice and the probe insertion orifice. In addition, the PDT delivery device may include an insertion probe having a stepped hollow cylinder positioned within the probe insertion orifice and within the tube retraction groove and having an insertion needle at a distal end. The PDT delivery device may include a fiber locking mechanism and a probe release mechanism selectively movable between an unlock position and a lock position. Also, the PDT delivery device may include a probe retraction mechanism releasably coupled to the insertion probe. Further, the PDT delivery device may include a retraction trigger coupled to the probe retraction mechanism to translate the insertion probe between an insertion position and a retraction position.

21 Claims, 10 Drawing Sheets

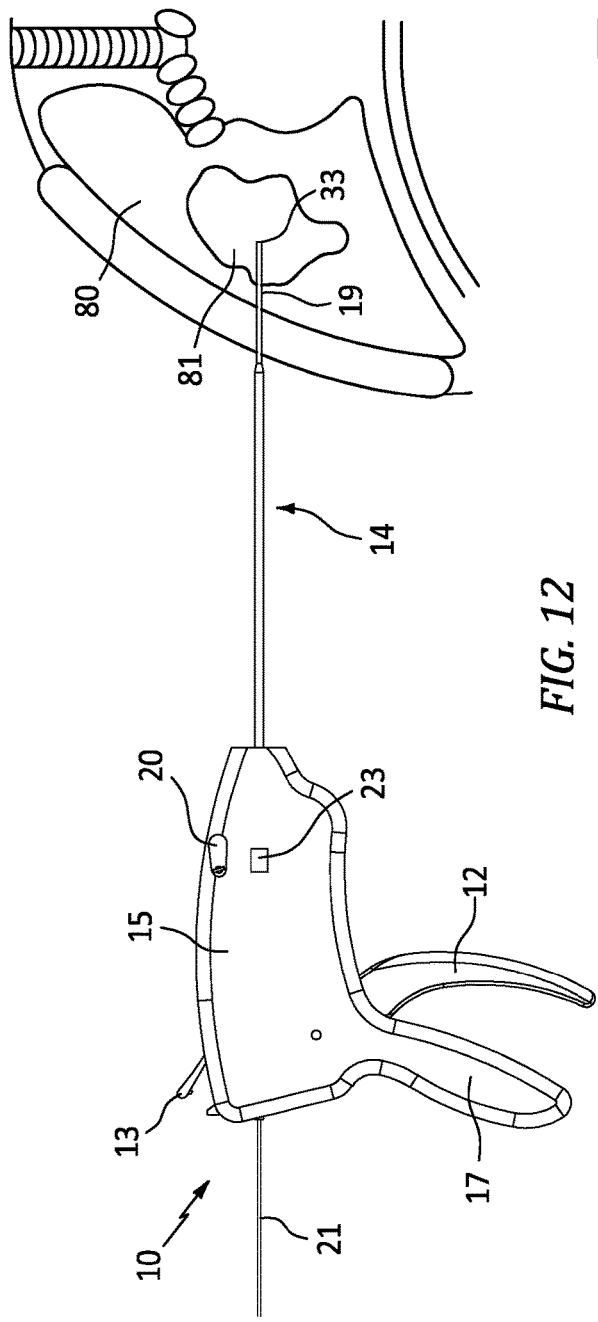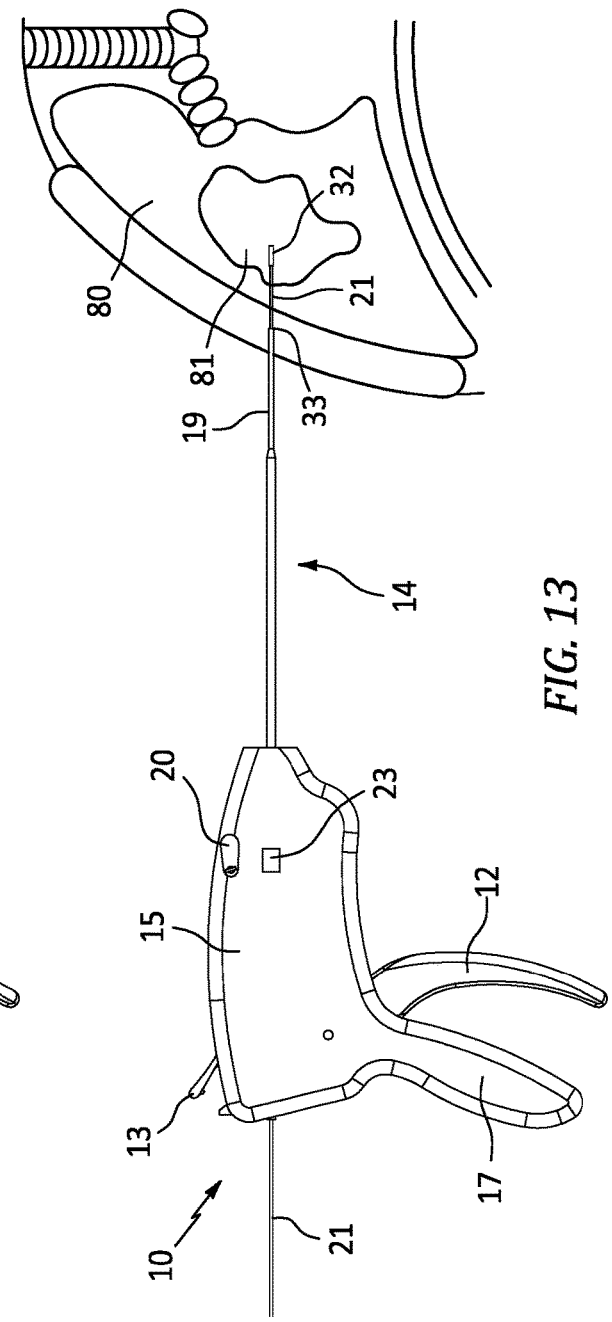
FIG. 12
FIG. 13

INTERSTITIAL PHOTODYNAMIC THERAPY PROBE DELIVERY DEVICE

CROSS REFERENCE TO RELATED APPLICATIONS

This application claims the benefit of Patent Cooperation Treaty Patent Application Serial No. PCT/US2023/60070 filed 04 Jan. 2023. The disclosure of this application is incorporated herein by reference in its entirety.

BACKGROUND

Field of Disclosure

The present disclosure relates to photodynamic therapy and more specifically to an interstitial photodynamic therapy (PDT) light delivery device and methods for interstitial delivery of PDT light therapy.

Description of the Related Art

PDT light therapy can be used for the treatment of conditions in multiple ways. For example, some light therapies involve the delivery of a therapeutic light through a fiber optic device placed proximal to or within a target tumor or cancerous tissue. It has proven difficult to accurately deliver the therapeutic light to a target area of a patient using the devices and methods found in the prior art.

What is needed is a PDT delivery device and method that solves the problems of the prior art.

SUMMARY

In one general aspect, a PDT delivery device may include a housing including a handle, a fiber lock orifice positioned on a back end, a probe insertion orifice positioned on a front end and a tube retraction groove positioned between the fiber lock orifice and the probe insertion orifice. The PDT delivery device may also include an insertion probe having a stepped hollow cylinder positioned within the probe insertion orifice and within the tube retraction groove and having an insertion needle at a distal end. Device may furthermore include a fiber locking mechanism positioned within fiber lock orifice and within the housing. Device may in addition include a probe release mechanism positioned in the housing and selectively movable between an unlock position and a lock position. Device may moreover include a probe retraction mechanism positioned within the housing and releasably coupled to the insertion probe. Device may also include a retraction trigger coupled to the probe retraction mechanism to translate the insertion probe between an insertion position and a retraction position.

Implementations may include one or more of the following features. The PDT delivery device where the insertion probe includes a bevel point at a distal end of the insertion needle. The PDT delivery device where the probe retraction mechanism may include a drive wheel coupled to the retraction trigger, a probe release mechanism having a swing arm pivotably attached to the housing, a biasing wheel rotatably mounted to the swing arm, a release mechanism coupled to the swing arm configured to actuate the swing arm between a lock position and a release position, and where the insertion probe is secured between the drive wheel and the biasing wheel in the lock position and where the insertion probe released from the biasing wheel in the release position. The PDT delivery device where the probe retraction mechanism further may include a drive ratchet wheel coupled to the drive wheel, a locking pawl engaged with the drive ratchet wheel configured to prevent rotation of the drive wheel in a forward direction, a drive pawl coupled to the retraction trigger engaged with the drive ratchet wheel, where the probe retraction mechanism is configured to rotate the drive wheel in a rearward direction when the insertion probe stop is in the unlock position, the swing arm is in the lock position and the retraction trigger is actuated, and where the insertion probe is retracted toward the back end of the housing into the retraction position within the tube retraction groove. The PDT delivery device may include an optical delivery fiber having a delivery tip at a distal end, a light emitter positioned on the delivery tip of the optical delivery fiber, and where the optical delivery fiber is positioned within the fiber locking mechanism, the tube retraction groove and the insertion probe and the delivery tip is positioned within the insertion needle in the insertion position. The PDT delivery device where the delivery tip is ejected from the insertion needle in the retraction position. The PDT delivery device where the optical delivery fiber is configured to be coupled to a therapy light source and the light emitter is configured to emit a therapy light to a target area of a patient. The PDT delivery device where the light emitter is a cylindrical light diffuser configured to radiate the therapy light in an isotropic cylindrical pattern. The PDT delivery device may include a spring cavity positioned in the housing adjacent to and axially aligned with the fiber lock orifice, a tapered cavity positioned in the housing adjacent to and axially aligned with the spring cavity and further adjacent to and axially aligned with the tube retraction groove, a retention wall formed between the tapered cavity and the spring cavity, the fiber locking mechanism may include a snubbing mechanism having a hollow main tube body having a first end positioned in the fiber lock orifice a second end having a collet positioned within the tapered cavity in the housing, a shoulder positioned between the first end and the second end, a biasing cup positioned against the shoulder, a fiber release spring captured between the biasing cup and the retention wall, a fiber lock trigger pivotably positioned within the housing and positioned against the biasing cup. The PDT delivery device may include the fiber lock trigger is selectively positionable between a fiber release position and a fiber lock position, the fiber release spring biases the biasing cup against the fiber lock trigger in the fiber release position, an inner diameter of the collet is configured to slidably engage an optical delivery fiber in the fiber release position, and where the fiber lock trigger translates the collet into the tapered cavity in the fiber lock position and releasably locks the optical delivery fiber in the collet.

In one general aspect, a method may include providing a PDT delivery device having a housing including a handle, a fiber lock orifice positioned on a back end, a probe insertion orifice positioned on a front end and a tube retraction groove positioned between the fiber lock orifice and the probe insertion orifice, an insertion probe having a stepped hollow cylinder having an insertion needle at a distal end, a fiber locking mechanism positioned within the fiber lock orifice and within the housing, an probe release mechanism positioned in the housing and selectively movable between an unlock position and a lock position, a probe retraction mechanism positioned within the housing and releasably coupled to the insertion probe, and a retraction trigger coupled to the probe retraction mechanism. The method may also include positioning the insertion probe stop into the lock position. The method may furthermore include positioning the fiber locking mechanism into an unlock position. The method may in addition include inserting a proximal end of the insertion probe into the probe insertion orifice and within the tube retraction groove and against the insertion probe stop. The method may moreover include inserting a delivery tip of an optical delivery fiber into fiber locking mechanism. The method may also include threading the delivery tip through the insertion probe and at least partially through the insertion needle.

Implementations may include one or more of the following features. The method may include piercing a tissue of a patient with the insertion needle and delivering a distal end of the insertion needle to a target area of the patient and positioning the delivery tip at the distal end of the insertion needle. The method may include coupling a distal end of the optical delivery fiber to a therapy light source. The method may include positioning the fiber locking mechanism into a lock position, positioning the insertion probe stop into the unlock position, actuating the retraction trigger and translating the insertion probe into a retraction position within the housing, and ejecting the delivery tip into the target area of the patient. The method may include transmitting a therapy light from the therapy light source to the delivery tip, emitting the therapy light from the delivery tip, and delivering a dose of therapy light to the target area. The method where the delivery tip may include a cylindrical light diffuser, the method may include delivering the dose of therapy light to the target area in an isotropic cylindrical pattern. The method may include guiding the insertion needle to the target area using an imaging device. The method may include developing a treatment plan that includes a total dose of therapy light and delivering the total dose of therapy light to the target area. The method where the treatment plan further includes a photosensitizing drug, the method may include delivering the photosensitizing drug to the patient. The method may include positioning the fiber locking mechanism into an unlock position and removing the insertion needle from the target area of the patient.

BRIEF DESCRIPTION OF THE DRAWINGS

So that the manner in which the above-recited features of the present disclosure can be understood in detail, a more particular description of the disclosure, briefly summarized above, may be had by reference to implementations, some of which are illustrated in the appended drawings. It is to be noted, however, that the appended drawings illustrate only typical implementations of this disclosure and are therefore not to be considered limiting of its scope, for the disclosure may admit to other equally effective implementations.

FIG. 12 is an illustration of a PDT delivery device in accordance with the present disclosure; and FIG. 13 is an illustration of a PDT delivery device in accordance with the present disclosure.

DETAILED DESCRIPTION

Figure 1:
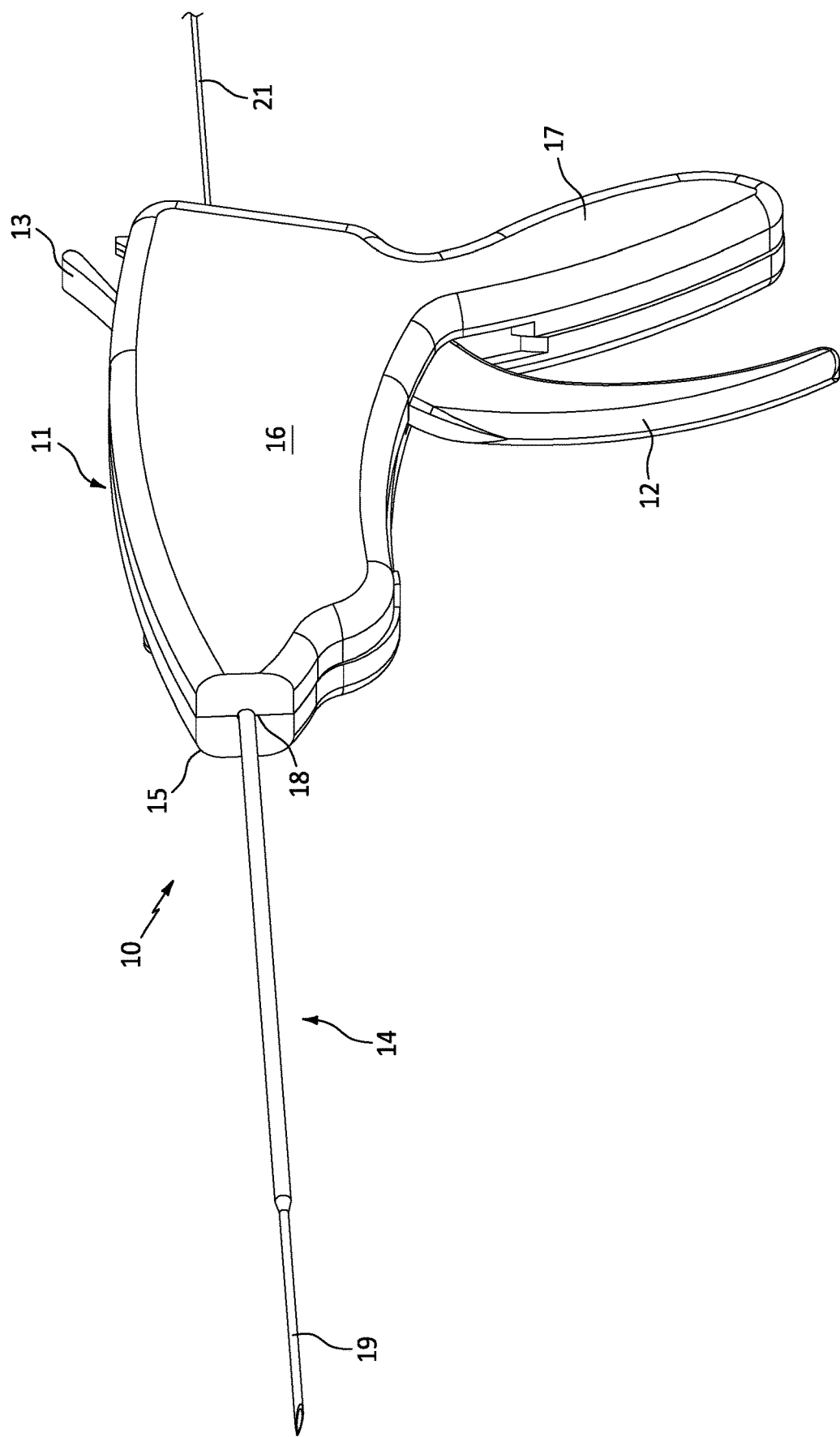
FIG. 1 is a left hand frontal isometric view of a PDT delivery device in accordance with the present disclosure.
Figure 2:
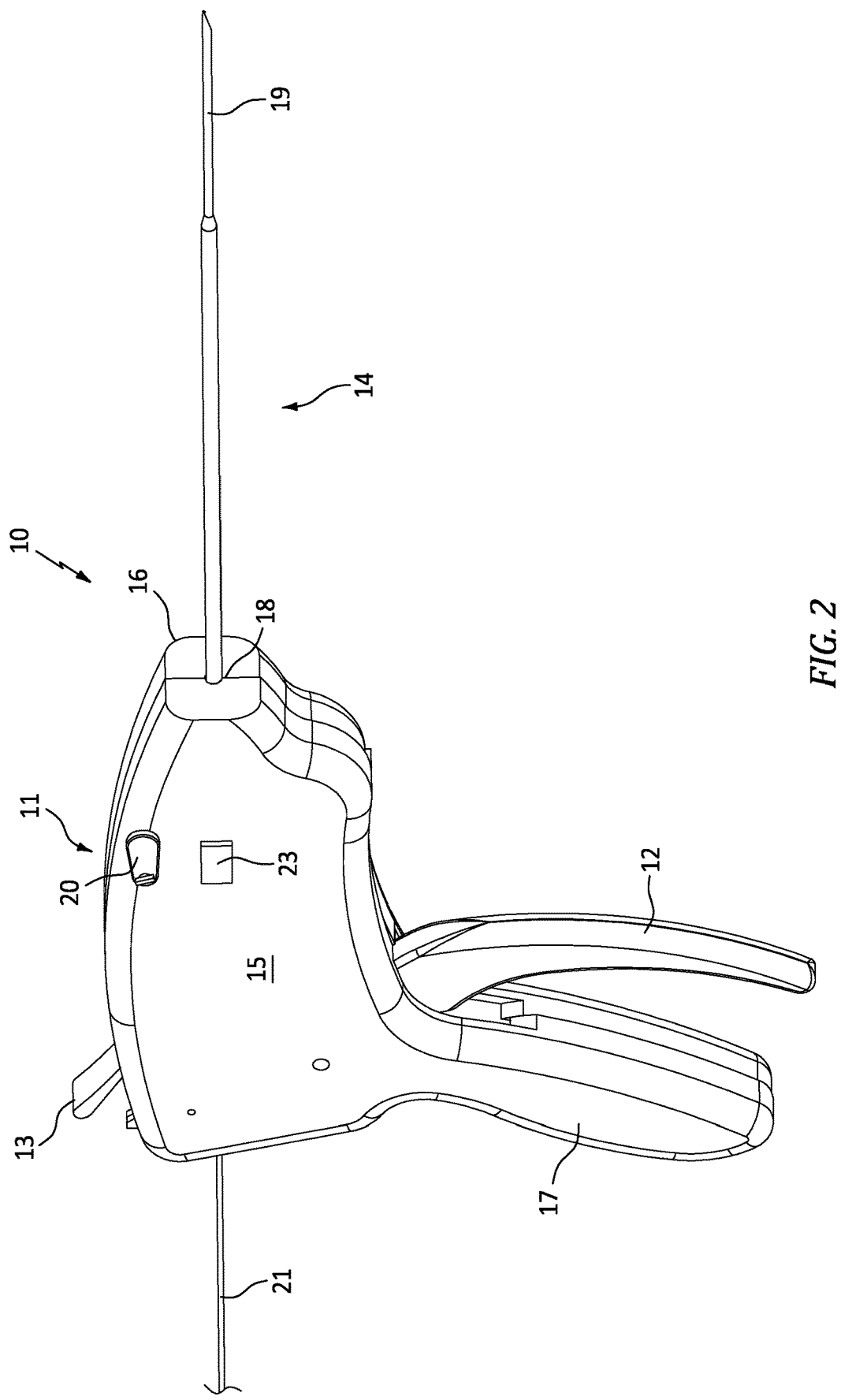
FIG. 2 is a right hand frontal isometric view of a PDT delivery device in accordance with the present disclosure.
Figure 3:
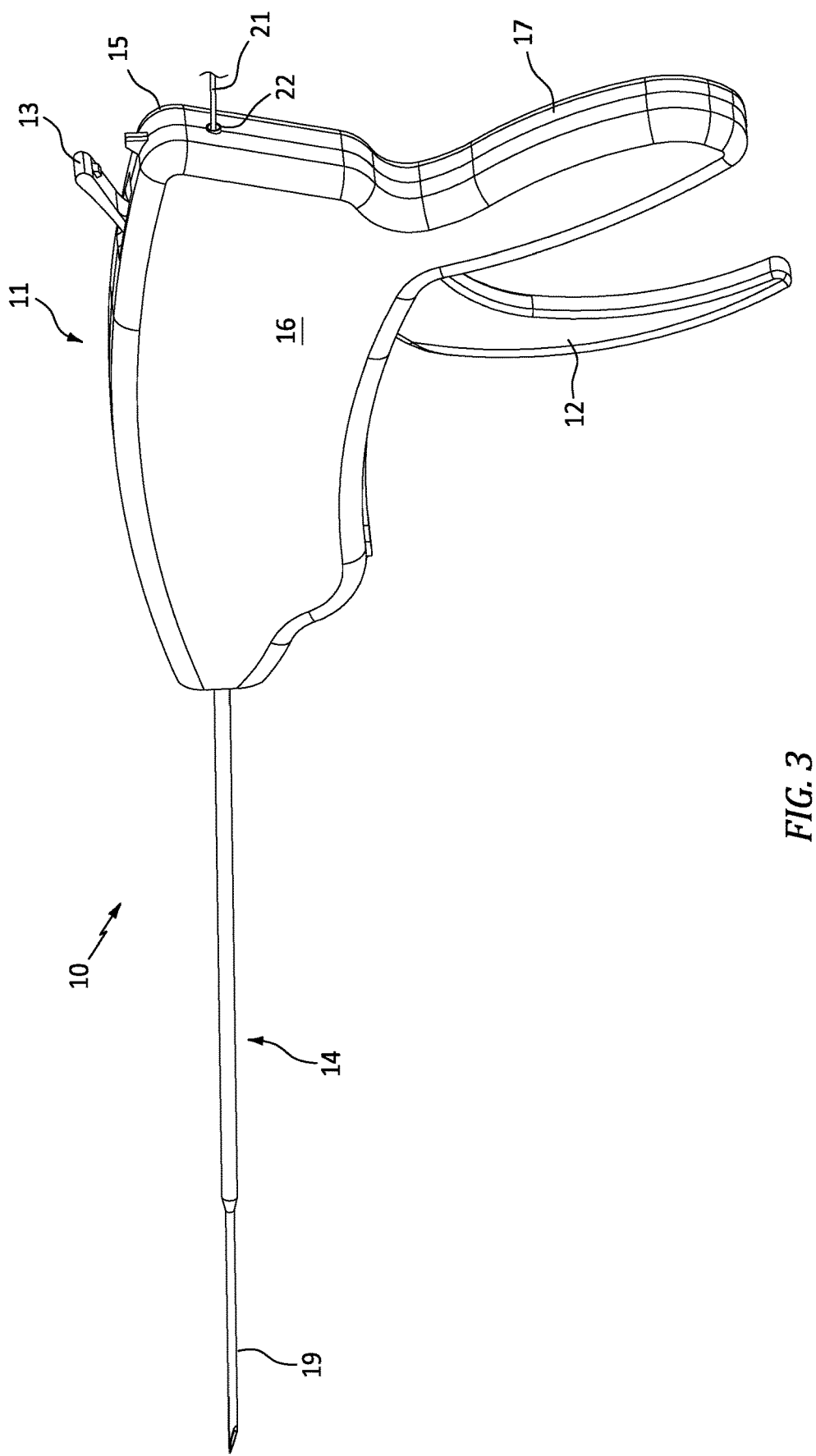
FIG. 3 is a left hand rear isometric view of a PDT delivery device in accordance with the present disclosure.

In the following detailed description, reference is made to the accompanying drawings, which form a part hereof, and within which are shown by way of illustration specific implementations by which the examples described herein may be practiced. It is to be understood that other implementations may be utilized and structural changes may be made without departing from the scope of the disclosure.

Implementations of the present disclosure provide systems and methods of delivering PDT light at a delivery tip of a delivery optical fiber interstitially at a target tissue of a patient using a handheld PDT delivery device during the procedure. In such procedures a photosensitizing drug is typically administered to a patient, which photosensitizing drug is absorbed in higher concentrations in a cancerous portion of tissue. In a surgical procedure for a patient having a cancerous tumor, the photosensitizing drug can be administered prior to surgery. As disclosed herein before, a cancerous portion of tissue absorbs the photosensitizing drug in higher concentrations than a non-cancerous portion of tissue. Now, with reference to FIGS. 1-4, there is shown a PDT delivery gun 10 for use in such a procedure comprised of housing 11, retraction trigger 12, fiber lock lever 13 and insertion probe 14. Housing 11 is comprised of a right portion 15 and a left portion 16 and includes handle 17 and probe insertion orifice 18 positioned in a front end of housing 11. Insertion probe 14 further includes insertion needle 19 positioned at its distal end. Right portion 15 further includes insertion probe release lever 20 and probe stop lever 23. Also shown in the figures is optical delivery fiber 21 within PDT delivery gun 10 positioned within fiber lock orifice 22 in a back end of housing 11. Housing 11 can be comprised of a plastic, a surgical metal or a combination of any suitable materials. Insertion probe 14 can be comprised of a surgical metal.

Figure 5:
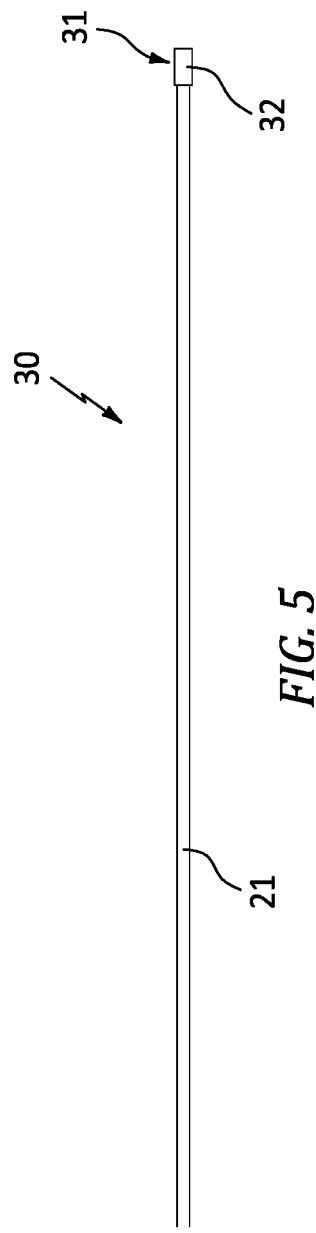
FIG. 5 is a side view of an optical delivery fiber and light emitter in accordance with the present disclosure.

Now with reference to FIG. 5, there is shown an implementation of a PDT delivery fiber 30 in accordance with the current disclosure. PDT delivery fiber 30 can comprise optical delivery fiber 21 terminating in delivery tip 31. Optical delivery fiber 21 can comprise any optical fiber suitable for transmitting PDT therapy light from a source (not shown) to delivery tip 31 including a single mode fiber or a mutli-mode fiber and can have an outside diameter of about 5 mm. Delivery tip 31 includes light emitter 32 which can be comprised of a light diffuser configured to emit PDT therapy light delivered by optical delivery fiber 21 at a target area of a patient as will be disclosed in more detail herein after. Delivery tip 31 can be configured to emit PDT therapy light only at its distal end or along the entire length of the tip. In some implementations light emitter 32 of delivery tip 31 can comprise a cylindrical light diffuser configured to radiate therapy light in an isotropic cylindrical pattern.

Figure 6:
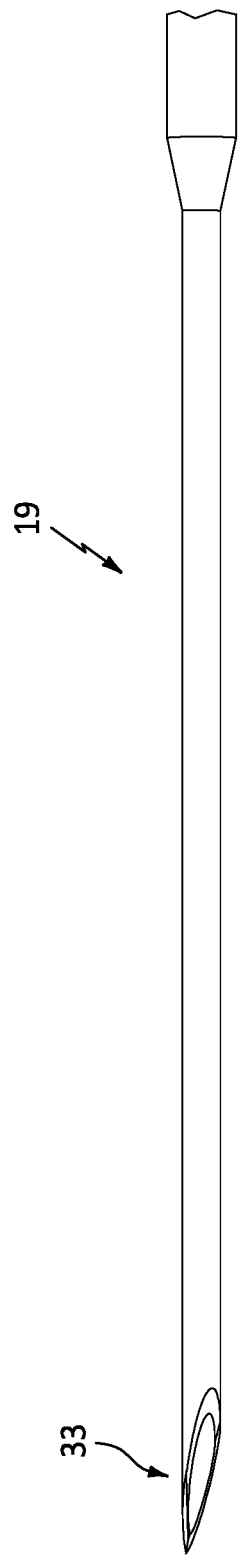
FIG. 6 is a left hand side view of an insertion needle of a PDT delivery device in accordance with the present disclosure.
Figure 7:
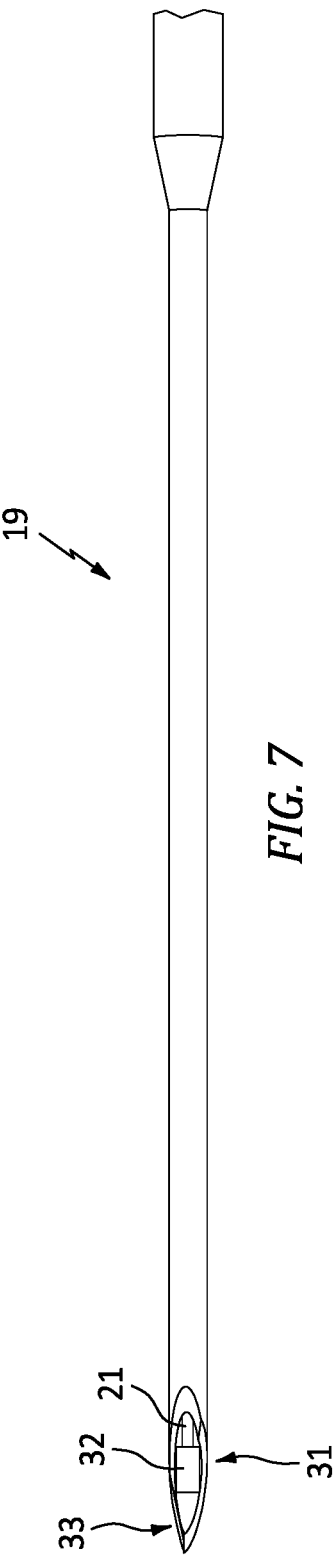
FIG. 7 is a bottom view of an insertion needle of a PDT delivery device in accordance with the present disclosure.

Referring next to FIG. 6, there is shown a side view of insertion needle 19 with PDT delivery fiber 30 in a retracted position. Insertion needle 19 comprises a hollow tube structure and includes bevel point 33 positioned at its distal end. Bevel point 33 is formed in the distal end of insertion needle 19 to produce a sharp point and edge for insertion into the tissue of a patient. In some implementations insertion probe 14 is a stepped hollow cylinder and can have an outer diameter of less than 3 mm and an internal diameter of nominally 1.5 mm and insertion needle 19 can have the same internal diameter but can have an outer diameter of less than 2 mm to facilitate insertion into the tissue of a patient. In FIG. 7 a bottom view of insertion needle 19 is shown with delivery tip 31 in an extended position with light emitter 32 and a portion of PDT delivery fiber 21 positioned within bevel point 33 of the distal end of insertion needle 19 prior to a PDT procedure as will be disclosed in more detail herein after.

Figure 4:
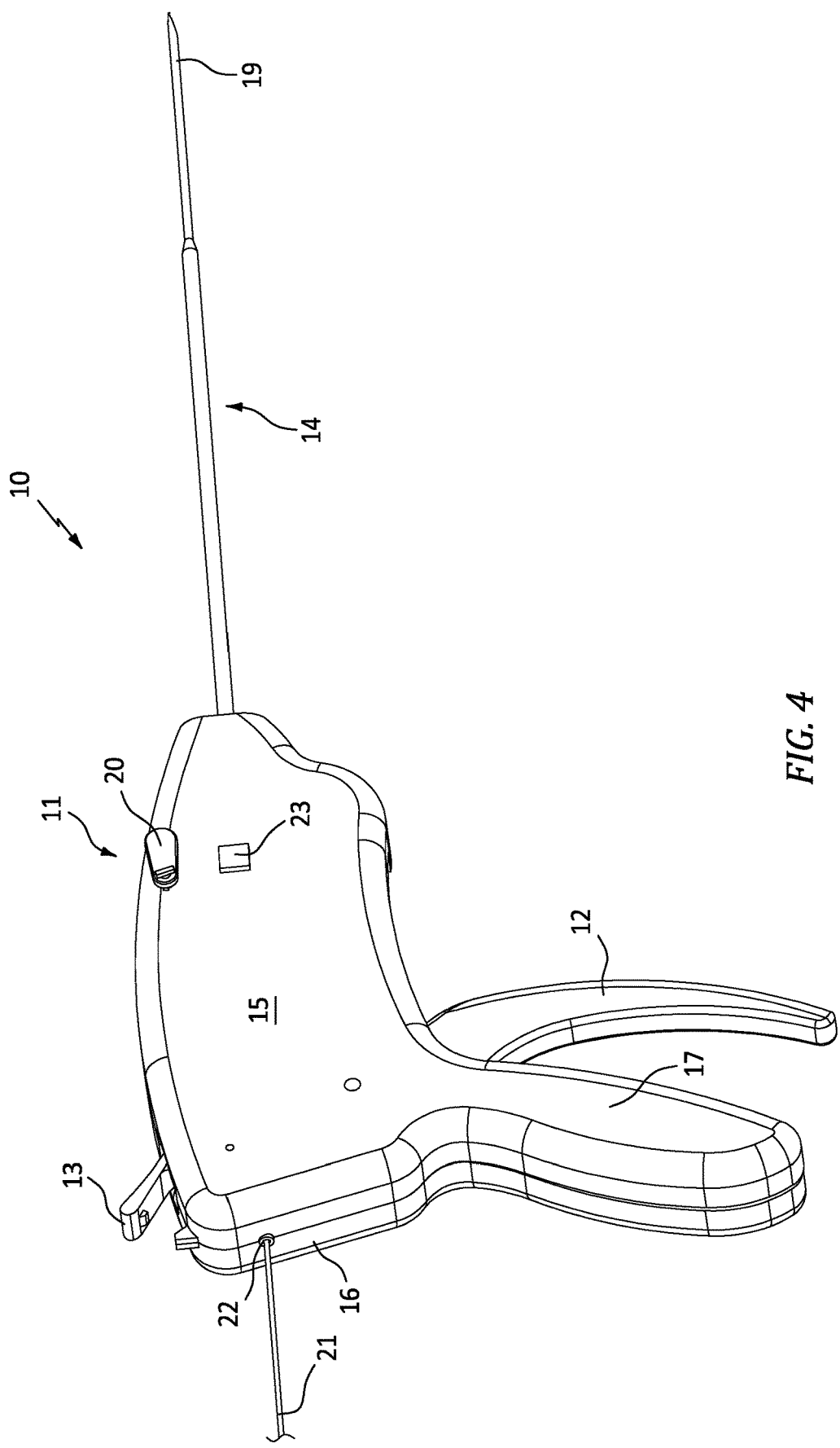
FIG. 4 is a right hand rear isometric view of a PDT delivery device in accordance with the present disclosure.
Figure 8:
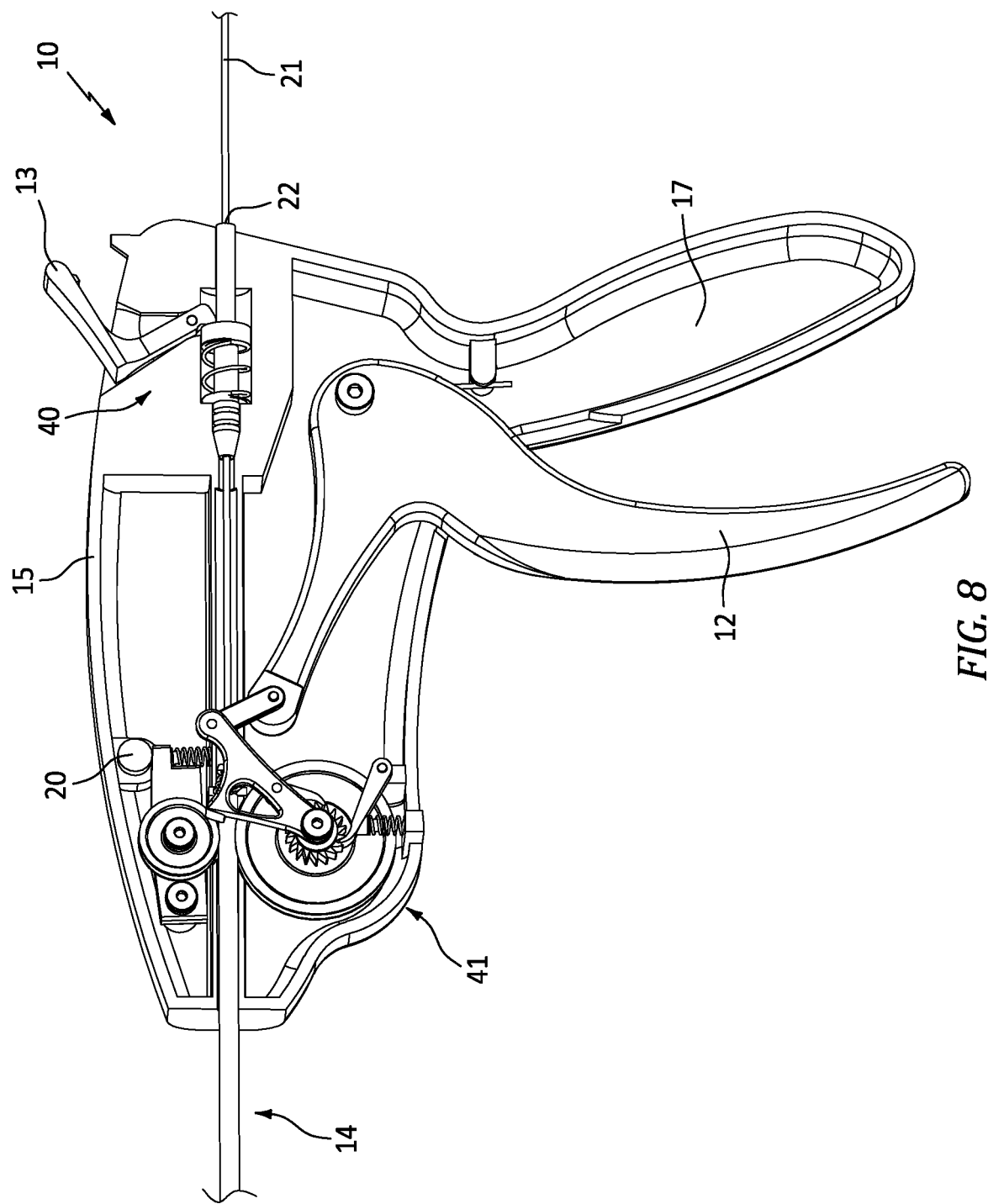
FIG. 8 is an inside view of a right hand portion of a PDT delivery device in accordance with the present disclosure.
Figure 9:
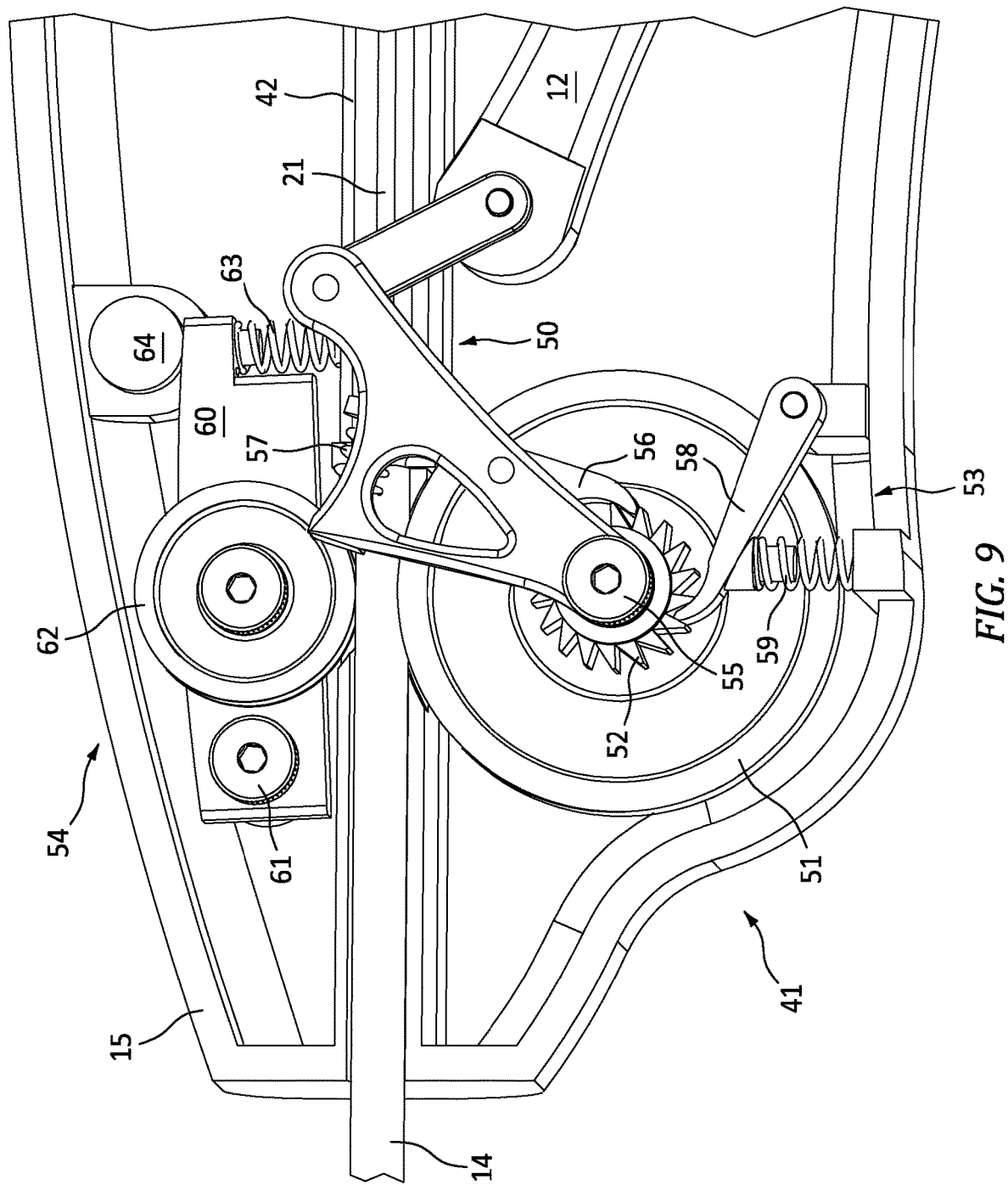
FIG. 9 is a detail view of a probe retraction mechanism and a probe release mechanism of a PDT delivery device in accordance with the present disclosure.

Now referring to FIG. 8 there is shown an internal view of right portion 15 of PDT delivery gun 10 including fiber locking mechanism 40 and probe retraction mechanism 41. Optical delivery fiber 21 is positioned inside of fiber lock orifice 22 and passes through the interior of fiber locking mechanism 40 and into the internal diameter of insertion probe 14. With reference to FIG. 9 there is shown the detail of probe retraction mechanism 41 which includes lever system 50, drive wheel 51, locking pawl mechanism 53 and probe release mechanism 54. Lever system 50 rotatably coupled to retraction trigger 12 on a first end and rotatably positioned about pivot bolt 55 on a second end. Drive wheel 51 can be comprised of any suitable material and can include a semi-circular groove on its outer diameter having a diameter that is similar to the outer diameter of insertion probe 14. Drive wheel 51 includes drive ratchet wheel 52 fixedly attached thereto with the drive wheel rotatably mounted to right portion by pivot bolt 55. Lever system 50 further includes drive pawl 56 rotatably mounted thereto and biased against drive ratchet wheel 52 by drive spring 57. Locking pawl mechanism 53 is comprised locking pawl 58 rotatably mounted to right portion 15 and biased against drive ratchet wheel 52 by locking spring 59 to prevent rotation of the drive wheel. Probe release mechanism 54 is comprised of swing arm 60 pivotably mounted to right portion 15 by pivot bolt 61, biasing wheel 62 rotatably mounted to the swing arm, swing arm spring 63 which biases the swing arm against release cam 64 with the release cam coupled to release lever 20 (FIG. 4). Actuation of release lever 20 positions probe release mechanism 54 into an unlock position. Similar to drive wheel 51, biasing wheel 62 can include a semi-circular groove on its outer diameter having a diameter that is similar to the outer diameter of insertion probe 14 and in some implementations the semi-circular grooves can comprise a rubber material having a coefficient of friction.

Figure 10:
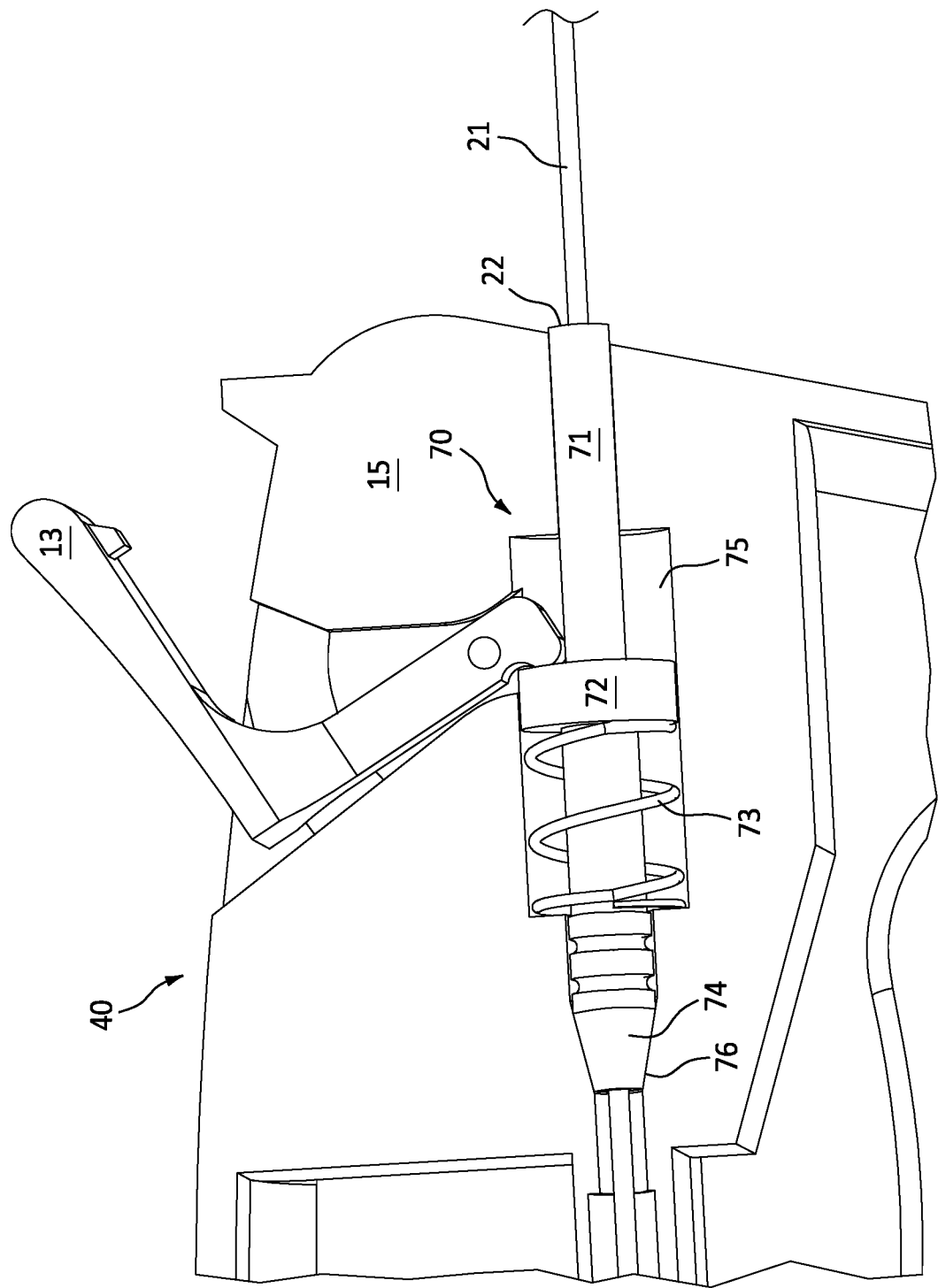
FIG. 10 is a detail view of a fiber locking mechanism of a PDT delivery device in accordance with the present disclosure.

With reference to FIG. 10 there is shown the detail of fiber locking mechanism 40 in a fiber release position which comprises fiber lock lever 13 pivotably mounted to right portion 15 and snubbing mechanism 70. Snubbing mechanism 70 comprises hollow main tube body 71, a biasing cup 72, a fiber release spring 73, and a collet 74. Snubbing mechanism 70 is positioned within cavities of right portion 15 wherein fiber release spring 73 is captured between a retention wall of spring cavity 75 and biasing cup 72 to force the biasing cup against fiber lock lever 13 in the released position. Hollow main tube body 71 and collet 74 include an internal diameter that is larger than optical delivery fiber 21 such that the optical delivery fiber can be freely translated within the internal diameter in the released position. Collet 74 is frustoconical shaped and is comprised of a conformable material, such as a rubber material, and has at least two circumferentially spaced segments at its conical end and is positioned within tapered cavity 76 and includes a shoulder against which biasing cup 72 is positioned. With optical delivery fiber 21 positioned within the internal diameter of hollow main tube body 71 and collet 74 a user can actuate fiber locking mechanism 40 into a fiber lock position. To do so, the user pushes fiber lock trigger 13 in a downward direction, forcing biasing cup to translate within spring cavity 75 against the shoulder of collet 74 and forcing the collet against tapered cavity 76. It should be appreciated by those skilled in the art that the at least two segments of collet 74 are forced against optical delivery fiber 21 releasably capturing the optical delivery fiber in the collet. With specific reference to FIG. 11, there is shown an interior section of right portion 15 including insertion probe stop 24. Now with reference back to FIG. 2, insertion probe stop 24 is slidably positioned within a slot in right portion 15 and is actuated between a lock position (shown) and a release position (not shown) by probe stop lever 23. In operation, a user starts by inserting insertion probe 14 into probe insertion orifice 18 and further within retraction mechanism 41 between drive wheel 51 and biasing wheel 62 and against insertion probe stop 24 in the lock position. It should be appreciated by those skilled in the art that insertion probe stop 24 limits the translation distance of insertion probe 14 within housing 11. Further, with fiber locking mechanism 40 in a released position, a user inserts delivery fiber 30 (FIG. 5) through fiber lock orifice 22, hollow main tube body 71, collet 74, tube retraction groove 42 of housing 11, and insertion probe 14.

Now referring to FIG. 12, there is shown an example of insertion needle 19 of PDT delivery gun 10 positioned within a tumor 81 of a human lung 80. In this example tumor 81 is a target area for treatment using PDT techniques and can be located by any known method or imaging device such as a computerized tomography (CT) scan. The CT scan can be used to guide insertion needle 19 using other known techniques such as ultrasound imaging. The operation of PDT delivery gun 10 can best be described with reference to FIGS. 1-13. In operation, a proximal end of optical delivery fiber 21 is coupled to a PDT therapy light source (not shown) and delivery tip 31 is inserted through fiber lock orifice 22 on the back side of PDT delivery gun 10 by a user. The user further inserts delivery tip 31 through tube retraction groove 42 and into the inner diameter of the proximal end of insertion probe 14 inside of housing 11 of PDT delivery gun 10 and further inserts the delivery tip into a portion of insertion needle 19. The user then actuates fiber lock trigger 13 to releasably hold optical delivery fiber 21 in position within the insertion probe 14 and inserts insertion needle 19 interstitially into the target area of tumor 81 of a patient (FIG. 12). It should be noted that insertion probe 14 captured between biasing wheel 62 and drive wheel 51 is locked in place (prevented from rotating in the forward direction), relative to housing 11, by locking pawl engaged within drive ratchet wheel 52 and is prevented from translating into housing 11 by insertion probe stop 24 in the lock position putting the insertion probe in the insertion position. The user can verify that the distal end of insertion needle 19 is positioned at the location of the target area using, for example, the aforementioned ultrasound imaging and CAT scans. Once the position of the distal end of insertion needle 19 is verified, the user actuates probe stop lever 23 to position probe stop 24 into the release position. The user can then grasp handle 17 and retraction trigger 12 and actuate the retraction trigger to urge it in the direction of the handle and engaging probe retraction mechanism 41. In engaging probe retraction mechanism 41 drive pawl 56 causes drive wheel 51 to rotate in the clockwise direction and thereby translating insertion probe in a rearward direction along tube retraction groove 42 further inside housing 11 and moves insertion needle 19 out of tumor 81 (FIG. 13) and into the retraction position within the housing. The user can use multiple actuations of retraction trigger 12 to translate a greater portion of insertion probe 19 in a rearward direction within housing 11. Once insertion needle 19 is retracted from tumor 81 the light emitter 32 of delivery tip 31 is ejected from the needle and is exposed within tumor 81 at the target location. With light emitter 32 of delivery tip 31 at the target location the user can then activate a PDT therapy light source coupled to optical delivery fiber 21 and deliver the PDT light interstitially to tumor 81 through light emitter 32. The user can, following a treatment plan, deliver the PDT light interstitially to tumor 81 for a predetermined length of time in order to deliver a predetermined total dose of PDT therapy light to tumor 81. The user can then remove delivery tip 31 from tumor 81 and from the patient's body by grasping optical delivery fiber 21 and pulling it in a direction opposite of the insertion direction.

Figure 11:
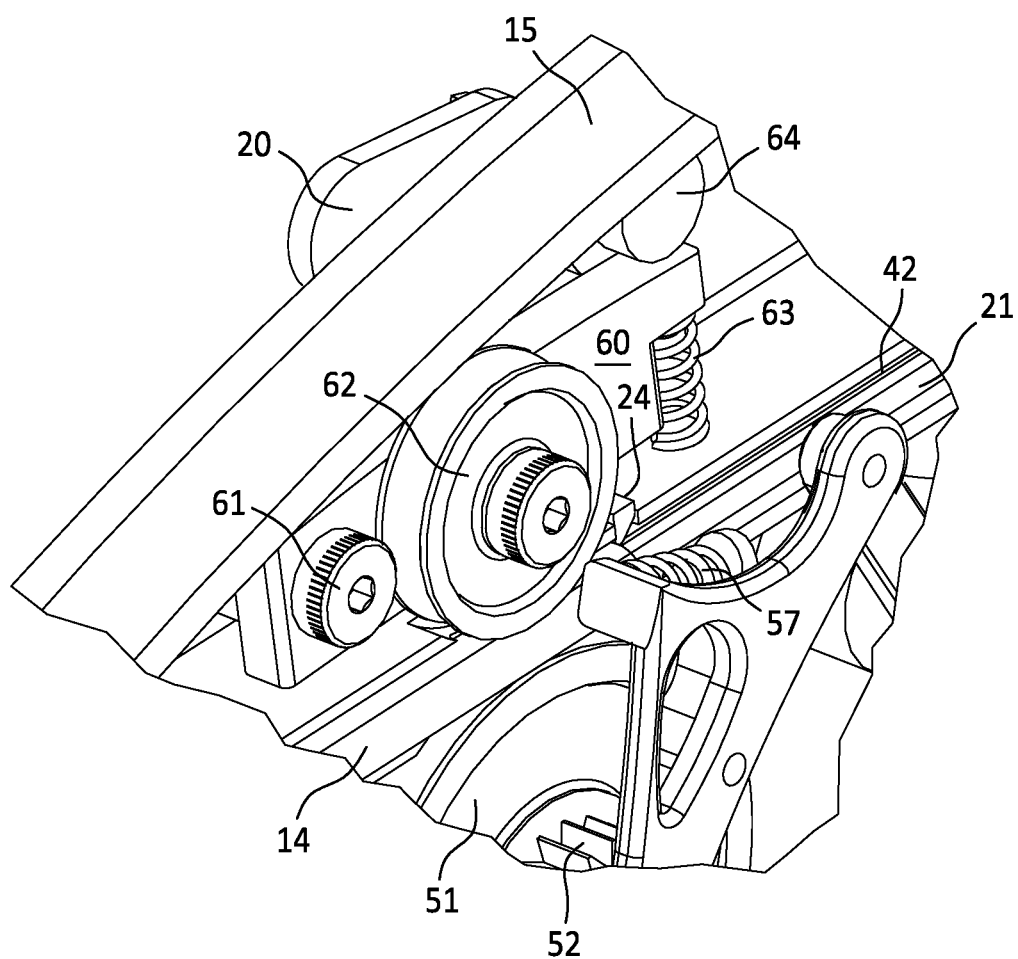
FIG. 11 is a detail view of a probe release mechanism of a PDT delivery device in accordance with the present disclosure.

If other target areas within tumor 81 require treatment, PDT delivery gun 10 can be prepared for subsequent use. Referring to FIGS. 2, 4,8 and 11, the user can actuate release lever 20 which allows biasing wheel 62 of probe release mechanism to be lifted off insertion probe 14. The user can then translate insertion probe 14 from the retracted position (FIG. 13) to the extended position (FIGS. 8, 11). The user can then return release lever 20 forcing biasing wheel to releasably lock insertion probe 14 between the biasing wheel and drive wheel 51 and can further actuate probe stop lever 23 to position probe stop 24 into the lock position.

The foregoing disclosure provides illustration and description but is not intended to be exhaustive or to limit the implementations to the precise form disclosed. Modifications may be made in light of the above disclosure or may be acquired from practice of the implementations. As used herein, satisfying a threshold may, depending on the context, refer to a value being greater than the threshold, greater than or equal to the threshold, less than the threshold, less than or equal to the threshold, equal to the threshold, and/or the like, depending on the context. Although particular combinations of features are recited in the claims and/or disclosed in the specification, these combinations are not intended to limit the disclosure of various implementations. In fact, many of these features may be combined in ways not specifically recited in the claims and/or disclosed in the specification.

Although each dependent claim listed below may directly depend on only one claim, the disclosure of various implementations includes each dependent claim in combination with every other claim in the claim set. No element, act, or instruction used herein should be construed as critical or essential unless explicitly described as such. Also, as used herein, the articles "a" and "an" are intended to include one or more items and may be used interchangeably with "one or more." Further, as used herein, the article "the" is intended to include one or more items referenced in connection with the article "the" and may be used interchangeably with "the one or more." Furthermore, as used herein, the term "set" is intended to include one or more items (e.g., related items, unrelated items, a combination of related and unrelated items, and/or the like), and may be used interchangeably with "one or more." Where only one item is intended, the phrase "only one" or similar language is used. Also, as used herein, the terms "has," "have," "having," or the like are intended to be open-ended terms. Further, the phrase "based on" is intended to mean "based, at least in part, on" unless explicitly stated otherwise. Also, as used herein, the term "or" is intended to be inclusive when used in a series and may be used interchangeably with "and/or," unless explicitly stated otherwise (e.g., if used in combination with "either" or "only one of").

What is claimed is:

1. A photodynamic therapy (PDT) delivery device comprising:
   a housing including a handle, a fiber lock orifice positioned on a back end, a probe insertion orifice positioned on a front end and a tube retraction groove positioned between the fiber lock orifice and the probe insertion orifice;
   an insertion probe comprising a stepped hollow cylinder positioned within the probe insertion orifice and within the tube retraction groove and having an insertion needle at a distal end;
   a fiber locking mechanism positioned within fiber lock orifice and within the housing;
   a probe release mechanism positioned in the housing and selectively movable between an unlock position and a lock position;
   a probe retraction mechanism positioned within the housing and releasably coupled to the insertion probe; and
   a retraction trigger coupled to the probe retraction mechanism to translate the insertion probe between an insertion position and a retraction position.

2. The PDT delivery device of claim 1 wherein the insertion probe includes a bevel point at a distal end of the insertion needle.

3. The PDT delivery device of claim 1 wherein the probe retraction mechanism comprises:
   a drive wheel coupled to the retraction trigger;
   a probe release mechanism comprising:
      a swing arm pivotably attached to the housing;
      a biasing wheel rotatably mounted to the swing arm;
      a release mechanism coupled to the swing arm configured to actuate the swing arm between a lock position and a release position; and wherein the insertion probe is secured between the drive wheel and the biasing wheel in the lock position and wherein the insertion probe is released from the biasing wheel in the release position.

4. The PDT delivery device of claim 3 wherein the probe retraction mechanism further comprises:
   a drive ratchet wheel coupled to the drive wheel;
   a locking pawl engaged with the drive ratchet wheel configured to prevent rotation of the drive wheel in a forward direction;
   a drive pawl coupled to the retraction trigger engaged with the drive ratchet wheel;
   wherein the probe retraction mechanism is configured to rotate the drive wheel in a rearward direction when an insertion probe stop is in the unlock position, the swing arm is in the lock position and the retraction trigger is actuated; and
   wherein the insertion probe is retracted toward the back end of the housing into the retraction position within the tube retraction groove.

5. The PDT delivery device of claim 1 further comprising:
   a spring cavity positioned in the housing adjacent to and axially aligned with the fiber lock orifice;
   a tapered cavity positioned in the housing adjacent to and axially aligned with the spring cavity and further adjacent to and axially aligned with the tube retraction groove;

a retention wall formed between the tapered cavity and the spring cavity;

the fiber locking mechanism comprises:
- a snubbing mechanism comprising:
  - a hollow main tube body comprising:
    - a first end positioned in the fiber lock orifice
    - a second end comprising a collet positioned within the tapered cavity in the housing;
    - a shoulder positioned between the first end and the second end;
  - a biasing cup positioned against the shoulder;
  - a fiber release spring captured between the biasing cup and the retention wall;
  - a fiber lock trigger pivotably positioned within the housing and positioned against the biasing cup.

6. The PDT delivery device of claim 5 further comprising:
the fiber lock trigger is selectively positionable between a fiber release position and a fiber lock position;
the fiber release spring biases the biasing cup against the fiber lock trigger in the fiber release position;
an inner diameter of the collet is configured to slidably engage an optical delivery fiber in the fiber release position; and
wherein the fiber lock trigger translates the collet into the tapered cavity in the fiber lock position and releasably locks the optical delivery fiber in the collet.

7. The PDT delivery device of claim 4 further comprising:
an optical delivery fiber having a delivery tip at a distal end;
a light emitter positioned on the delivery tip of the optical delivery fiber; and
wherein the optical delivery fiber is positioned within the fiber locking mechanism, the tube retraction groove and the insertion probe and the delivery tip is positioned within the insertion needle in the insertion position.

8. The PDT delivery device of claim 7 wherein the delivery tip is ejected from the insertion needle in the retraction position.

9. The PDT delivery device of claim 7 wherein the optical delivery fiber is configured to be coupled to a therapy light source and the light emitter is configured to emit a therapy light to a target area of a patient.

10. The PDT delivery device of claim 9 wherein the light emitter is a cylindrical light diffuser configured to radiate the therapy light in an isotropic cylindrical pattern.

11. A method of delivering photodynamic therapy (PDT) to a patient comprising:
providing a PDT delivery device comprising:
- a housing including a handle, a fiber lock orifice positioned on a back end, a probe insertion orifice positioned on a front end and a tube retraction groove positioned between the fiber lock orifice and the probe insertion orifice;
- an insertion probe comprising a stepped hollow cylinder having an insertion needle at a distal end;
- a fiber locking mechanism positioned within the fiber lock orifice and within the housing;
- a probe release mechanism positioned in the housing and selectively movable between an unlock position and a lock position;
- a probe retraction mechanism positioned within the housing and releasably coupled to the insertion probe; and
- a retraction trigger coupled to the probe retraction mechanism;

positioning an insertion probe stop into a lock position;
positioning the fiber locking mechanism into an unlock position;
inserting a proximal end of the insertion probe into the probe insertion orifice and within the tube retraction groove and against the insertion probe stop;
inserting a delivery tip of an optical delivery fiber into the fiber locking mechanism; and
threading the delivery tip through the insertion probe and at least partially through the insertion needle.

12. The method of delivering photodynamic therapy to a patient of claim 11 further comprising:
piercing a tissue of a patient with the insertion needle and delivering a distal end of the insertion needle to a target area of the patient; and
positioning the delivery tip at the distal end of the insertion needle.

13. The method of delivering photodynamic therapy to a patient of claim 12 further comprising coupling a distal end of the optical delivery fiber to a therapy light source.

14. The method of delivering photodynamic therapy to a patient of claim 13 further comprising:
positioning the fiber locking mechanism into a lock position;
positioning the insertion probe stop into an unlock position;
actuating the retraction trigger and translating the insertion probe into a retraction position within the housing; and
ejecting the delivery tip into the target area of the patient.

15. The method of delivering photodynamic therapy to a patient of claim 14 further comprising:
transmitting a therapy light from the therapy light source to the delivery tip;
emitting the therapy light from the delivery tip; and
delivering a dose of therapy light to the target area.

16. The method of delivering photodynamic therapy to a patient of claim 15 wherein the delivery tip comprises a cylindrical light diffuser, the method further comprising delivering the dose of therapy light to the target area in an isotropic cylindrical pattern.

17. The method of delivering photodynamic therapy to a patient of claim 15 further comprising guiding the insertion needle to the target area using an imaging device.

18. The method of delivering photodynamic therapy to a patient of claim 15 further comprising:
developing a treatment plan that includes a total dose of therapy light; and
delivering the total dose of therapy light to the target area.

19. The method of delivering photodynamic therapy to a patient of claim 15 further comprising:
positioning the fiber locking mechanism into an unlock position; and
removing the insertion needle from the target area of the patient.

20. The method of delivering photodynamic therapy to a patient of claim 19 further comprising removing the delivery tip from the target area of the patient.

21. The method of delivering photodynamic therapy to a patient of claim 18 wherein the treatment plan further includes a photosensitizing drug, the method further comprising delivering the photosensitizing drug to the patient.

* * * * *